(12) United States Patent
Rousseau

(10) Patent No.: US 6,755,867 B2
(45) Date of Patent: Jun. 29, 2004

(54) HERNIA REPAIR PROSTHESIS AND METHOD

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 428 days.

(21) Appl. No.: 09/752,066

(22) Filed: Dec. 29, 2000

(65) Prior Publication Data

US 2001/0027347 A1 Oct. 4, 2001

Related U.S. Application Data

(63) Continuation-in-part of application No. 09/540,793, filed on Mar. 31, 2000, now Pat. No. 6,425,924.

(51) Int. Cl.[7] .................................................. A61F 2/02
(52) U.S. Cl. .............................. 623/23.64; 623/23.72; 623/11.11
(58) Field of Search .......................... 623/23.64, 23.72, 623/23.75, 11.11; 606/151–153

(56) References Cited

U.S. PATENT DOCUMENTS

| | | |
|---|---|---|
| 2,671,444 A | 3/1954 | Pease, Jr. |
| 3,054,406 A | 9/1962 | Usher |
| 4,347,847 A | 9/1982 | Usher |
| 4,452,245 A | 6/1984 | Usher |
| 4,561,434 A | 12/1985 | Taylor |
| 4,744,364 A | 5/1988 | Kensey |
| 4,852,568 A | 8/1989 | Kensey |
| 4,854,316 A * | 8/1989 | Davis ........................ 128/334 |
| 5,021,059 A | 6/1991 | Kensey et al. |
| 5,059,205 A | 10/1991 | El-Nounou et al. |
| 5,061,274 A | 10/1991 | Kensey |
| 5,108,420 A | 4/1992 | Marks |
| 5,116,357 A | 5/1992 | Eberbach |
| 5,122,155 A | 6/1992 | Eberbach |
| 5,141,515 A | 8/1992 | Eberbach |
| 5,147,374 A | 9/1992 | Fernandez |
| 5,147,384 A | 9/1992 | La Rocca |
| 5,192,302 A | 3/1993 | Kensey et al. |
| 5,254,133 A | 10/1993 | Seid |
| 5,258,000 A | 11/1993 | Gianturco |
| 5,290,217 A | 3/1994 | Campos |
| 5,356,432 A | 10/1994 | Rutkow et al. |
| 5,368,602 A | 11/1994 | De La Torre |
| 5,370,650 A | 12/1994 | Tovey et al. |
| 5,397,331 A | 3/1995 | Himpens et al. |
| 5,425,740 A | 6/1995 | Hutchinson, Jr. |
| 5,456,720 A | 10/1995 | Schultz et al. |
| 5,545,178 A | 8/1996 | Kensey et al. |
| 5,634,931 A | 6/1997 | Kugel |
| 5,686,090 A * | 11/1997 | Schilder et al. ............. 424/423 |
| 5,716,408 A | 2/1998 | Eldridge et al. |
| 5,741,297 A | 4/1998 | Simon |
| 5,743,917 A * | 4/1998 | Saxon ...................... 623/11.11 |
| 5,769,864 A | 6/1998 | Kugel |
| 5,824,082 A | 10/1998 | Brown |
| 5,916,225 A | 6/1999 | Kugel |
| 5,944,738 A * | 8/1999 | Amplatz et al. ............. 606/213 |
| D416,327 S | 11/1999 | Kugel |
| 5,976,174 A * | 11/1999 | Ruiz .......................... 606/213 |
| 6,113,623 A * | 9/2000 | Sgro .......................... 606/215 |
| 6,113,641 A * | 9/2000 | Leroy et al. .............. 623/20.75 |
| 6,174,322 B1 * | 1/2001 | Schneidt ..................... 606/213 |
| 6,176,863 B1 * | 1/2001 | Kugel et al. ................ 606/151 |
| 6,180,848 B1 * | 1/2001 | Flament et al. .......... 623/11.11 |
| 6,214,029 B1 * | 4/2001 | Thill et al. ................. 606/213 |
| 6,241,768 B1 * | 6/2001 | Agarwal et al. ......... 623/11.11 |
| 6,270,515 B1 * | 8/2001 | Linden et al. .............. 606/213 |

FOREIGN PATENT DOCUMENTS

EP    0888756    1/1999

OTHER PUBLICATIONS

US 5,318,559, 6/1994, Mulhauser et al. (withdrawn)

* cited by examiner

Primary Examiner—David H. Willse
Assistant Examiner—Suzette J. Jackson

(57) ABSTRACT

A hernia repair prosthesis with an occlusive member for inserting into and/or backing the herniated tissue. An overlay sheet is attached to the occlusive member by a filament which permits the occlusive member and the overlay sheet to slide relative to one another along the filament allowing the maximal positioning of the overlay sheet to provide the best surgical attachment, orientation and alignment with the patient's anatomy.

22 Claims, 7 Drawing Sheets

HERNIA REPAIR PROSTHESIS AND METHOD

CROSS REFERENCE TO RELATED APPLICATION

This application is a continuation-in-part of application Ser. No. 09/540,793 filed on Mar. 31, 2000 now U.S. Pat. No. 6,425,924.

FIELD OF THE INVENTION

The present invention relates to an implantable hernia repair prosthesis and a method for reinforcing and repairing damaged tissue or muscle walls.

BACKGROUND OF THE INVENTION

Various prosthetic mesh materials have been proposed to reinforce the abdominal wall and to close abdominal wall defects utilizing different repair prostheses and methods of installation. The methods of executing a surgical repair can be segregated into two main approaches. The repair can be made exclusively from the anterior side (closest to the surgeon) of the defect by dissecting the sac free of the fascia and pressing it back into the pre-peritoneal space and providing permanent closure of the defect. The closure can be provided through the application of space filling prostheses and overlay patches (tension-free techniques) or can be accomplished through the use of sutures (tension techniques).

An example of a tension free anterior repair is to fold a sheet of surgical mesh fabric into a multi-layer cone configuration and then to insert the mesh plug into a hernia defect to occlude the void. Such a multi-layer prosthesis is inherently stiff and may not fully conform to variations in the contour of the defect, leaving gaps between the implant and the abdominal wall that potentially could lead to recurrent herniation. The stiff, multi-layered mesh plug also may be susceptible to kinking and buckling during placement.

U.S. Pat. No. 5,356,432, discloses an implantable prosthesis that is a conical plug formed of a knitted polypropylene monofilament mesh fabric. Longitudinal pleats are hot molded into the mesh body to enhance the flexibility of the conical implant, ideally allowing the implant to closely match the contour of the herniated opening when compressed within the defect. When the device is installed into a fascial defect, the tip of the conical shaped plug presses into and against the visceral sac, potentially enabling long-term erosion of the peritoneum and underlying viscera. The device, in one embodiment, has filler material incorporated into the interior of the formed mesh cone in an attempt to minimize contraction of the device during healing. As collagen scar tissue grows into the prosthetic material, the cross linking of the maturing collagen fibers causes the scar tissue (and encapsulated plug device) to contract. This contraction of scar tissue within the defect and plug causes the surrounding diseased tissue to be subjected to tension, thus enabling re-occurrence of the hernia along the edge of the conical plug. The use of the device requires the passage of a pre-expanded plug through the hernia defect and relies upon the radial expansion force of the single layer mesh cone and filler leaves to occlude the defect. Additionally, since the plug is secured in position by anchoring to the surrounding diseased tissue, the device may dislodge and migrate within the pre-peritoneal space.

Alternatively, a defect may be repaired through the use of posterior approaches that provide various prosthetic devices in the pre-peritoneal space to prevent the peritoneum from entering the fascial defect. These devices, in some cases, require the use of laparoscopic techniques and, in other cases, require the application of the prosthesis from a remote location under the defect to be repaired. Examples of posterior approaches are disclosed in U.S. Pat. Nos. 5,116,357, 5,254,133 and 5,916,225. However, in many cases, procedures utilizing such devices are complicated, in addition to requiring the use of general anesthesia and costly disposable instrumentation to support the laparoscopic surgery.

Accordingly, the prior art lacks an implantable hernia repair prosthesis for occluding and repairing damaged muscle and tissue wall ruptures, that is adaptable to irregularities in the shape of the defect, is simple to install, does not require the use of general anesthesia during installation and resists radial collapse due to tissue incorporation.

SUMMARY OF THE INVENTION

The limitations of the prior art are overcome by the present invention which includes a hernia repair prosthesis with an occlusive member for aiding in the occlusion of a defect in facia tissue. An overlay sheet of the prosthesis is surgically attachable to an anterior side of the facia tissue. A filament extending from a first point of attachment to the overlay sheet to a second point of attachment extends substantially parallel to the overlay sheet between the first and second points of attachment. The occlusive member is slideably attached to the filament to permit the occlusive member to assume a selected position relative to the overlay sheet between the first and second points of attachment.

DESCRIPTION OF THE FIGURES

For a better understanding of the present invention, reference is made to the following detailed description of various exemplary embodiments considered in conjunction with the accompanying drawings, in which.

DETAILED DESCRIPTION OF THE INVENTION

Figure 1:
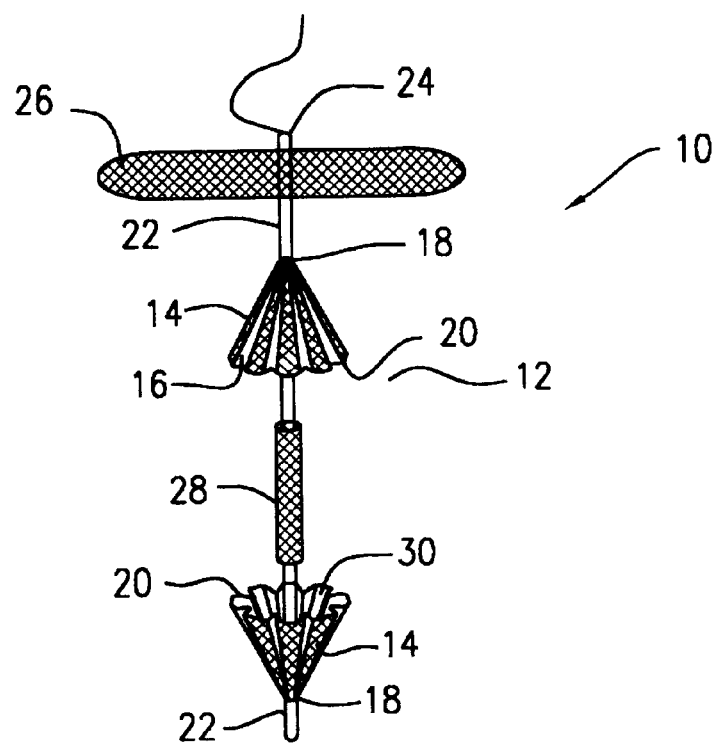
FIG. 1 is a perspective view of a prosthesis according to the present invention prior to assembly of all of its component parts.

The present invention provides implantable prostheses and methods for reinforcing and repairing weakened abdominal walls. The prostheses are formed of a biologically compatible, flexible and porous medical textile suitable for reinforcing tissue and occluding tissue defects. The implantable prostheses are indicated particularly for the repair of hernias in the abdominal cavity, including inguinal (direct and indirect), femoral, incisional and recurrent, and provide at least a partial posterior repair. The prostheses are able to be inserted easily in a stress-free condition into a fascia defect from an anterior approach and are capable of expanding radially, at least partially into the pre-peritoneal space, to substantially occlude and conform to the fascia wall of a fascia defect. Alternatively, a posterior approach may be used, if the surgeon prefers. The prostheses are suitable for the repair of varying sizes and shapes of hernias and can be anchored to the surrounding healthy tissue to prevent migration, thus extending beyond the edge of the defect on the anterior side of the defect. Other features of the present invention will become apparent from the following detailed description when taken in connection with the accompanying drawings that disclose multiple embodiments of the invention. The drawings are for the purpose of illustration only and are not intended as a definition of the limits of the invention.

The prostheses of the present invention comprise a hollow, radially-expandable member for placement within and occlusion of a fascia defect. By radially-expandable, it is meant that the cross sectional area of the member expands from an initial, non-expanded configuration having an initial cross sectional area, sized such that the member may be placed within a fascia defect in a stress-free condition, to a final, expanded configuration having a final cross sectional area greater than the initial cross sectional area and effective to occlude all of, or at least a substantial portion of, the fascia defect. This member can be manufactured out of biocompatible absorbable or non-absorbable material.

The prosthesis also comprises means for securing the prosthesis to the tissue wall. In certain embodiments, the means for securing comprises an overlay sheet of medical textile fixedly or maneuverably attached to the radially-expandable member, as depicted in the figures. When maneuverably, e.g. slidably, attached to the expandable member, the overlay sheet may be so-attached to the radially-expandable member by the use of a filament, or multiple filaments, passed through the looped suture or the proximal end of the expandable member and attached to the overlay patch at the terminal ends of the filament. Prostheses comprising such a slidably, or maneuverably, attached means for securing the prostheses to the tissue wall and a member for occluding the defect also are included within the scope of inventions disclosed herein. In such embodiments, the occluding member need not be radially-expandable, but need only be effective to occlude the defect. One of the advantages of such a prosthesis is that, once placed into the defect area, the securing means may be maneuvered such that attachment to stable or healthy tissue may be accomplished, thereby providing a more secure attachment to the tissue wall.

In other embodiments, the means for securing the prosthesis may be an integral part of the radially-expandable member. The prosthesis is passed into/through a defect in the fascial layer. The radially-expandable member then is collapsed axially, thus causing radial expansion of the radially-expandable member. The radial expansion of the radially-expandable member causes substantially complete occlusion of the fascial defect.

Slidable, or otherwise maneuverable, attachment of the radially-expandable member to the means for securing permits the overlay member to be maneuvered relative to the deployed expandable member and adjusted once placed within the fascia defect. This provides added benefit of being positionable, relative to the cord and other anatomical structures once in place, over conventional prostheses for repairing fascia defects which are fixedly attached to the means for securing to surrounding tissue, and are not capable of being adjusted once the prostheses are placed and fixed within the fascia defect.

While radial expansion of the member may be effected by means for radially-expanding the member as discussed and depicted herein, prostheses that are self-expanding, i.e. self-collapsing, when placed in position within the fascia defect are included within the scope of the present invention. Such devices may be constructed such that they will deploy, i.e. collapse axially and radially-expand to occlude the defect, when positioned within a defect in response to conditions of the body surrounding the defect. Preferably, a looped suture, passed longitudinally through the hollow cavity of the radially-expandable member along the axis thereof, may serve as a means for radially-expanding the member.

In certain embodiments of the invention, the radially-expandable member comprises opposing conical members fixedly attached one to the other at their respective bases, thus forming a cavity defined by the attached conical members. Each cone comprises pleated surfaces that increase the axial rigidity of the prosthesis, thus allowing the prosthesis to exert a radial expansion force, while ultimately maintaining the ability to conform to irregularities in the tissue or muscle wall surrounding the opening. One or more tubular structure of textile material may be contained within the cavity of the radially-expandable member to impart additional axial rigidity to the prosthesis, thus improving the handling characteristics during insertion into the defect. Tubular structure, as used herein, is meant to include those structures where the cross sectional configuration is tubular in nature. Tubular structure specifically includes cylindrical rolls of materials, e.g. meshes, where the cross section configuration is circular, as well as structures where the cross sectional configuration may be elliptical, triangular, rectangular, etc. The tubular structure also improves the radial expandability of the prosthesis when it is compressed axially and the cylinder collapses, ensuring a solid expansion of the prosthesis against and below the tissue or wall structure defining the defect.

The prostheses and radially-expandable member may be constructed from any suitable biologically compatible, flexible and porous medical textile known for reinforcing tissue and occluding tissue defects. Preferred mesh materials include knitted polypropylene monofilament mesh fabrics such as those available from Ethicon, Inc. under the Prolene trademark, as well as meshes available from Ethicon, Inc. under the Vicryl trademark. Other mesh materials useful in the invention include those available under the Marlex, Dacron, Teflon and Merselene trademarks. Alternatively, the desired effect of forcing tissue re-generation under the overlay patch can be accomplished through the selection of biocompatible absorbable materials for use in the fabrication of the expandable member. Examples of suitable materials are Vicryl and Panacryl sutures, available from Ethicon, Inc, and Polysorb suture, available from United States Surgical Corporation.

An exploded view of a prosthesis of the present invention is illustrated in FIG. 1. Prosthesis 10 comprises radially-expandable member 12, comprising first and second conical members 14. Each conical member 14 comprises longitudinal pleats 16 terminating at apex 18 and base 20 of each cone, respectively. The number and spacial relationship of longitudinal pleats 16 are effective to enhance the axial rigidity of the prosthesis and to allow the prosthesis to more closely match the contour of the fascia defect when compressed and placed within the defect. Preferably, the pleats are thermoformed into the mesh body. Looped suture 22, with a non-reversing knot 24, is passed through the inner diameter of opposing conical members 14. Sheet 26 of polypropylene mesh is fixedly attached to apex 18 of one of opposing conical members 14 through the use of looped suture 22. Sheet 26 is utilized to attach and secure the prosthesis to the surrounding healthy tissue. Optionally, prosthesis 10 may comprise one or more tubular structures 28 of polypropylene mesh contained within cavity 30 formed when opposing conical members 14 are attached at their respective bases 20. Tubular structure 28 provides additional axial rigidity to the prosthesis during handling and insertion of the device into the defect.

Suture 22 is passed through the inner diameter of the opposing conical members 14, passing from the apex of one through the apex of the other. Suture 22 then is looped and returned back through the inner diameter of the prosthesis in the opposite direction. Looped suture 22 is passed through the ends of the tubular structure 28 causing it to buckle, or collapse, when looped suture 22 is constricted during use. In the particular embodiment illustrated, both ends of looped suture 22 are passed through flat overlay sheet 26. Non-reversing knot 24 is tied in looped suture 22 and flat overlay sheet 26 is held in proximity to apex 18 of the upper one of the conical members 14. The dead tail of the knot 24 is trimmed to length. The finished prosthesis is subjected to sterilization prior to use.

Figure 2:
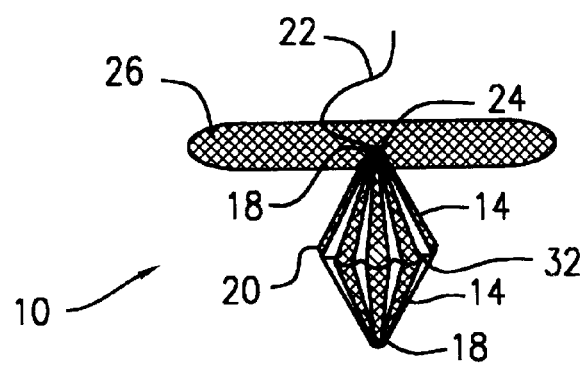
FIG. 2 is a perspective view of the assembled prosthesis depicted in FIG. 1.

The assembled prosthesis of FIG. 1 is illustrated in FIG. 2. Prosthesis 10 may be fabricated from any biocompatible medical woven, knitted or non-woven textile. In preferred embodiments, the prosthesis is fabricated from medical grade polypropylene mesh. Radially-expandable member 12 comprises conical members 14 fixedly attached one to the other at respective bases 20. Conical members 14 are configured to have an initial, non-expanded, maximum diameter that is substantially the same size or less than the diameter of the defect to be repaired. While the conical members 14 are shown in the figure to be identical in structure, embodiments in which one is taller than the other are contemplated by the invention. The conical members 14 are positioned in opposition one to the other and bases 20 are aligned. Once bases 20 are aligned, conical members 14 are fixedly attached to each other at respective bases 20. Bonding of the conical members 14 may be accomplished by stitching, welding or any other known form of fixable attachment, thus forming bond 32 about base 20. Preferably, prosthesis 10 comprises at least one flat sheet of mesh rolled into tubular structure 28 (FIG. 1) and permanently located within cavity 30 (FIG. 1) formed by fixedly attached conical members 14.

Tubular structure 28 is fabricated from a flat sheet of polypropylene mesh that, once rolled into cylindrical shape, can been secured about its circumference with suture. Alternatively, tubular structure 28 may be formed by rolling a flat sheet of mesh into the cylindrical configuration and welding, stitching or otherwise bonding the rolled sheet at the ends. Tubular structure 28 (FIG. 1) is disposed inside cavity 30 (FIG. 1) formed by fixedly attached opposing conical members 14 and extends axially from the internal apex 18 of one to the internal apex 18 of the other. Tubular structure 28 aids in providing axial rigidity to the prosthesis when it is inserted into the defect.

Figure 3:
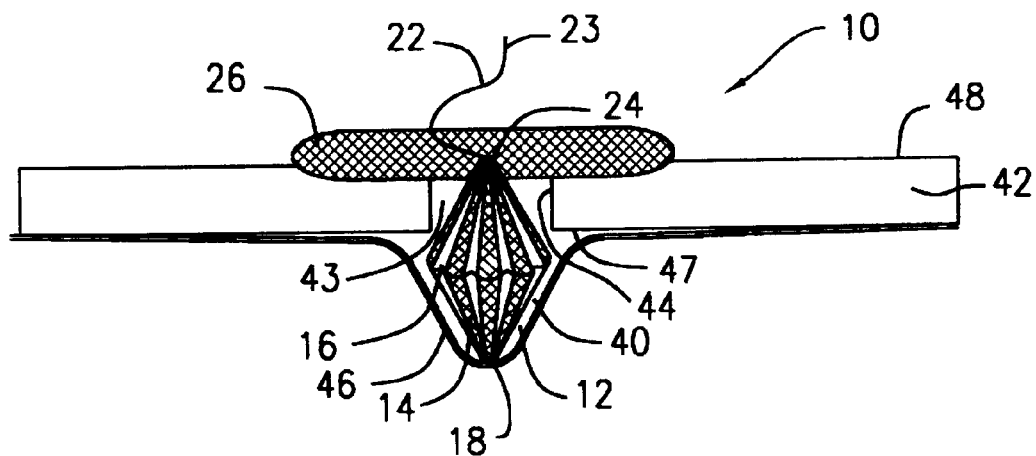
FIG. 3 is a perspective view of the prosthesis depicted in FIG. 2 when positioned within a defect in the fascia.
Figure 4:
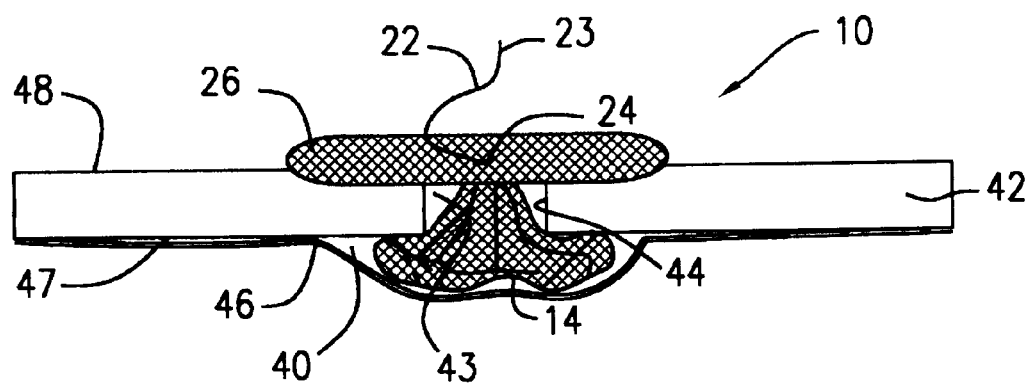
FIG. 4 is a perspective view of the prosthesis depicted in FIG. 3 after deployment, i.e. radial expansion, within the defect.

As shown in FIGS. 3 and 4, after hernia sac 40 has been dissected and/or ligated, prosthesis 10 is inserted into fascia defect 43. Once hernia sac 40 is free from walls 44 of defect 43 in fascia 42, hernia sac 40 is pressed back into the abdominal cavity. Apex 18 of the lower one of the conical members 14 is inserted into defect 43, causing peritoneum 46 to invert inwards into the abdominal cavity. Prosthesis 10 is inserted until mesh sheet 26 is flush with anterior side 48 of fascia 42. Free end 23 of suture 22 is pulled while prosthesis 10 is held in a forward position, i.e. flush with anterior side 48 of fascia 42. The tightening of suture 22 causes the opposing conical members 14 to be drawn together. The compression of the conical members 14 causes them to collapse axially onto themselves, thus causing the diameter of conical members 14 to expand radially and pleats 16 to open up or expand into a relatively flattened position. This same action causes tubular structure 28, located within cavity 30, to buckle, collapse and expand outward radially. Knot 24 is pulled until it is fully tightened.

Free end 23 of suture 22 may be provided with a needle to enable attachment of the prosthesis 10 to the surrounding healthy tissue by sewing overlay sheet 26 into place. Alternatively, free end 23 of suture 22 can be trimmed off after final deployment and the overlay patch can be attached in place through the use of additional sutures, or may remain in a flattened condition in the anterior space.

The prosthesis 10 is able to accommodate the spermatic cord structures since it is pleated. When it is expanded, it relies only on the radial expansion force generated from the compression of the opposing textile conical members 14 to enlarge their diameters, as opposed to the use of additional semi-rigid rings or other rigid or semi-rigid members. Preferably, prostheses of the present invention do not comprise such rigid or semi-rigid devices. This ensures that the device is fully compliant to the natural anatomical structures.

The final configuration of expanded prosthesis 10, as seen in FIG. 4, both occludes fascia defect 43 on posterior side 47 and is expanded to fill the inner diameter of defect 43 in wall 44. The expansion of radially expandable member 12 on posterior side 47 of defect 43 prevents peritoneum 46 from entering defect 43. Additionally, this posterior expansion ensures that the repair is secure from re-herniation through the defect, since the conical mesh is forced into a relatively flat condition. As the scar tissue grows into the flattened conical layers, it is compressed further in the axial direction by scar tissue contraction. With the inclusion of overlay patch 26, located on anterior side 48 of defect 43, it is virtually impossible for the device to migrate either anteriorly or posteriorly.

In another embodiment of the present invention as illustrated in FIGS. 5–9, the prosthesis is fabricated by cutting a biocompatible, medical textile, preferably polypropylene mesh, into a flat sheet. The sheet is provided with multiple slits, or continuous openings, extending across the width of the flat sheet for a distance effective to provide radial expansion of the radially-expandable member upon deployment of the prosthesis in a fascia defect and, thus, occlusion of the fascia defect. The slits do not extend to the edges of the sheet. The sheet also comprises as an integral part for fixedly attaching the prosthesis to tissue.

Figure 5:
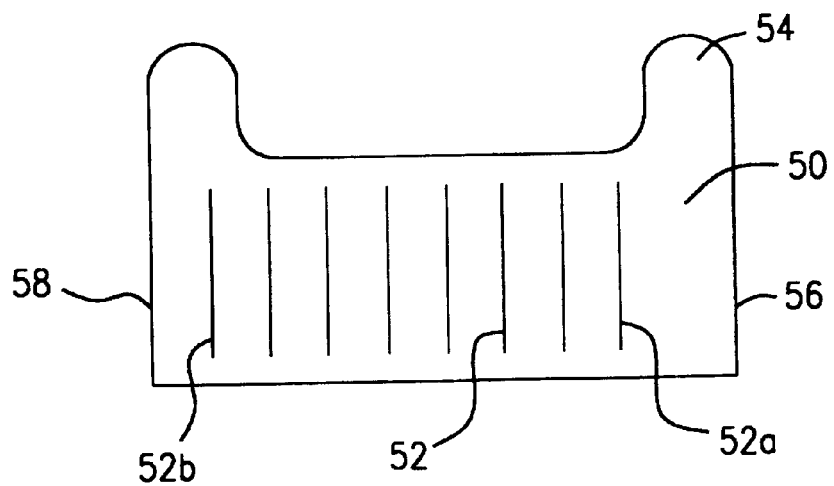
FIG. 5 is a top plan view of a sheet of mesh material used to construct another embodiment of the present invention.

As seen in FIG. 5, sheet 50 of mesh is provided with a plurality of slits 52 extending substantially, but not completely, across the width of sheet 50. The number, dimension and location of such slits will be effective to provide radial expansion of the radially-expandable member upon deployment within a defect. It is noted that the distance between slit 52a and edge 56 of sheet 50 is greater than the distance between slit 52b and edge 58 of sheet 50. While not required or essential to the invention, in certain embodiments, the distance between slit 52a and edge 56 is such that when the sheet is rolled onto itself to form a cylindrical roll, the inner-most layer of sheet material in the rolled cylinder is void of slits. In other words, the distance between slit 52a and edge 56 is equal to or greater than the inner circumference of the rolled cylinder. Sheet 50 also includes tabs 54, for use in subsequent fixed attachment of the prosthesis to tissue.

Figure 6A:
FIG. 6a is an end view of the mesh sheet depicted in FIG. 5 being rolled to form a radially-expandable member.
Figure 6B:
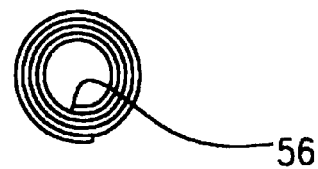
FIG. 6b is an end view of the mesh sheet depicted in FIG. 5 after being rolled to form a radially-expandable member.
Figure 7A:
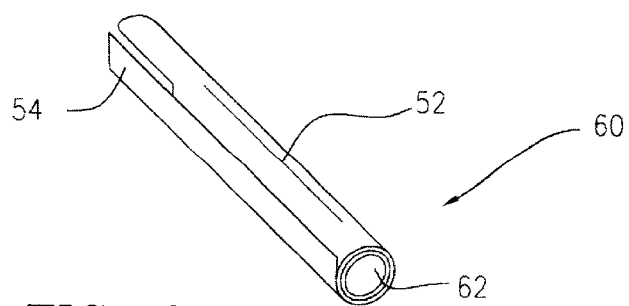
FIG. 7a is a perspective view of a radially-expandable member prepared from the mesh sheet depicted in FIG. 5.
Figure 7B:
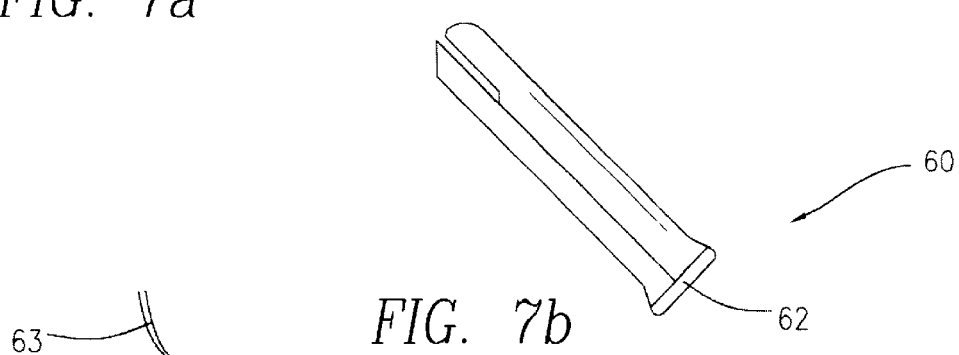
FIG. 7b is a perspective view of a radially-expandable member prepared from the mesh sheet depicted in FIG. 5.

As depicted in FIGS. 6a and 6b, sheet 50 is rolled such that edge 56 is rolled into the inner diameter of the cylindrical configuration. The roll is maintained in the cylindrical configuration through th use of tacking welds. sutures or others bonding means at each end of the roll, thus forming the radially-expanding member 60 for occluding a fascia end of the roll, illustrated in FIGS. 7a and 7b. End 62 of radially-expandable member 60 may be sealed closed by stitching, welding or bonding, for example.

Figure 8:
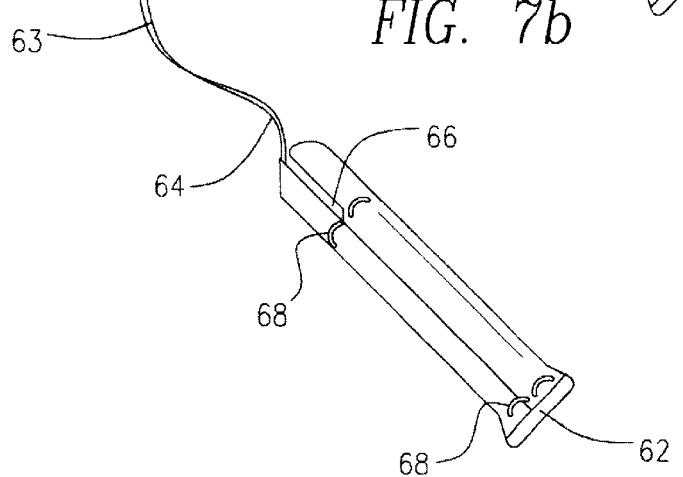
FIG. 8 is a perspective view of a prosthesis made from the radially-expandable member depicted in FIG. 7b.

As seen in FIG. 8, suture 64 is attached to end 62 of radially-expandable member 60 in purse-string arrangement 68, and then tightened and permanently knotted. Free end 63 of suture 64 is passed through the inner part of the rolled cylinder and is stitched around the circumference of open end 66 to form another purse-string arrangement 68. A non-reverse slipknot (not shown) is tied into the suture.

Figure 9:
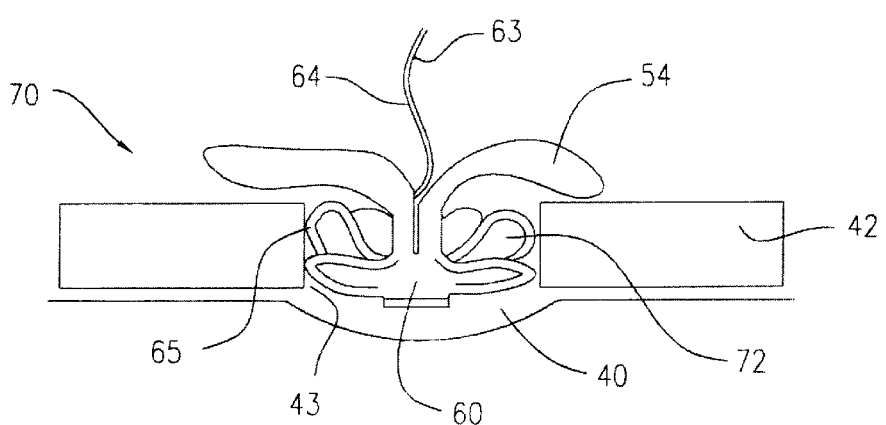
FIG. 9 is a perspective view of the prosthesis depicted in FIG. 8 after deployment, i.e. radial expansion, within a defect in the fascia.
Figure 10:
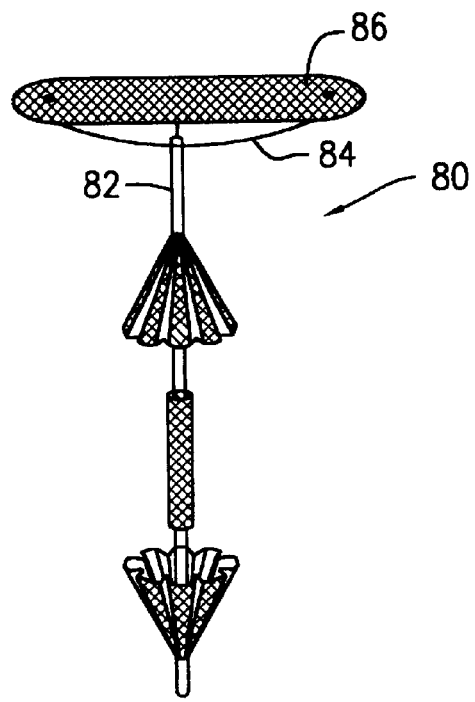
FIG. 10 is a perspective view of a prosthesis according to another embodiment of the present invention.
Figure 11:
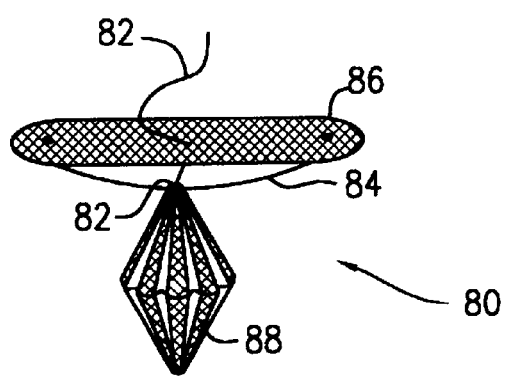
FIG. 11 is a perspective view of the assembled prosthesis depicted in FIG. 10.
Figure 12:
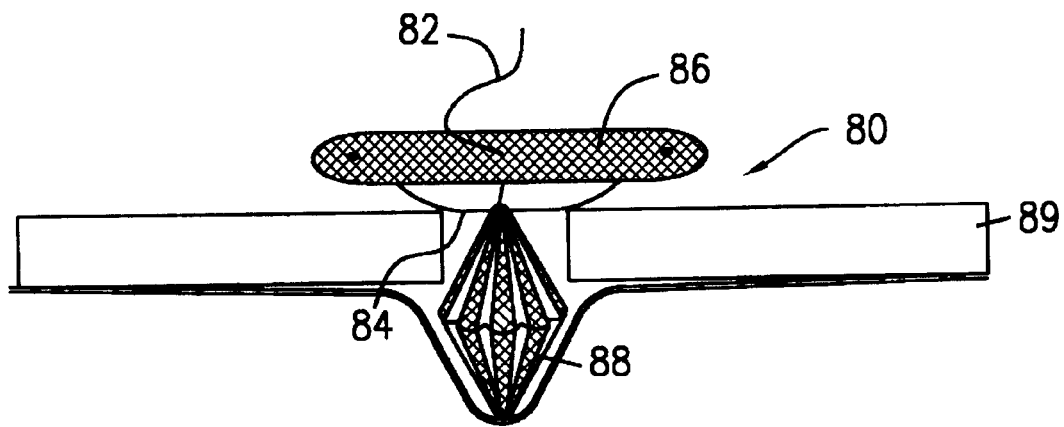
FIG. 12 is a perspective view of the prosthesis depicted in FIG. 11 when positioned within a defect in the fascia.

As depicted in FIG. 9, prosthesis 70 is placed into fascia defect 43 by pressing dissected/ligated hernia sac 40 into the abdominal cavity. Free end 63 of suture 64 is pulled while holding prosthesis 70 forward. As suture 64 is drawn, vertical slits 65 allow radially-expandable member 60 to collapse. Slits 65 buckle outwards, i.e. expand radially, forming overlapping leaves 72 that occlude defect 43. Tabs 54, located at the top of collapsed prosthesis 70, are used to fixedly attach the deployed prosthesis to surrounding healthy tissue.

Figure 13:
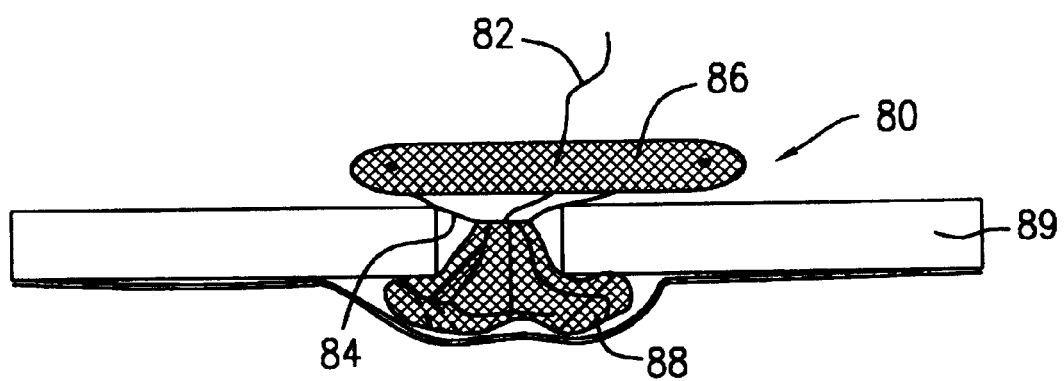
FIG. 13 is a perspective view of the prosthesis depicted in FIG. 12 after deployment, i.e. radial expansion, within the defect.

Referring to FIGS. 10–13, prosthesis 80 comprises overlay patch 86 slidably attached to radially-expandable member 88. As shown, filament 84 is passed through looped suture 82 and affixed at its terminal ends to overlay patch 86. When radial-expandable member 88 is placed in the defect, overlay patch 86 may be maneuvered to one side, as shown in FIG. 13, to effect attachment to fascia 89.

Figure 14:
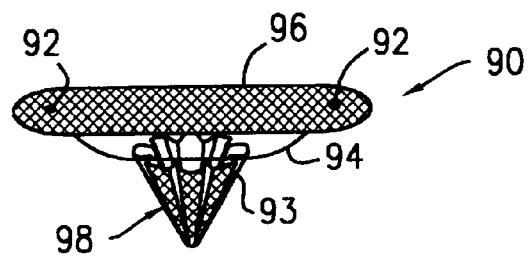
FIG. 14 is a perspective view of a prosthesis according to a further embodiment of the present invention.

FIG. 14 shows a prosthesis 90 having an overlay patch 96 slidably attached to a radially expandable member 98 (like the thermoformed expandable member 20 described above in reference to FIG. 1) by an elongated filament 94. The filament 94 is joined to the overlay patch 96 at two spaced points 91, 92, e.g., by tying, plastic welding or by being restrained from pulling through the overlay patch 96 material by knots or enlarged ends that exceed the size of the pores of the material of the patch 96. Intermediate the points of connection 91, 92, the filament 94 extends substantially parallel to the overlay patch 94 and is spaced therefrom to accommodate the portion of the radially expandable member 98 positioned between the filament 94 and the overlay patch 96. While a single filament 94 is shown, a plurality of parallel filaments 94 may be utilized. The radially expandable member 98 is preferably formed from surgical mesh material or other biocompatible filamentous material that has numerous openings therethrough, i.e., the spaces between adjacent filaments that are woven or compressed together to yield a mesh and/or felt-like textile. The filament 94 simply threads through the spaces between adjacent filaments that define the textile structure of the expandable member 98. In the alternative, in the case of a non-filamentous radial expandable member 98, e.g., one made from a continuous plastic film, the filaments can be passed through the film by providing holes in the film with a needle and then threading the filament(s) 94 through the holes. In either case, the radially expandable member 98 is moveable along the filament(s) 94 defining a motion "track" relative to the overlay patch 96.

In FIG. 14, the filament 94 passes through a cone-shaped, radially-expandable member 98 proximate the base 93 of the cone. Because the expandable member 98 is slidable on the filament 94, the expandable member 98 may be positioned relative to the overlay patch 96 to maximally conform to the anatomy of the patient and the surgical repair encountered. More particularly, the expandable member 98 may be inserted into the facia void and then the position of the overlay patch 96 may be adjusted to coincide with the position of maximally effective surgical attachment, viz., to be amenable to attaching the overlay patch 96 to healthy tissue, to bridge over weak, unhealthy tissue, and also to conform to the patients' local anatomical shape. The relative slidability of the overlay patch 96 and the expandable member 98 does not impede the expandable member 98 from collapsing and expanding to fill the breach in the facia (i.e., the filament 94 retains the overlay patch 96 in association with the expandable member 98, but does not restrict the expansion of the expandable member 98). The overlay patch 96 may have any desired shape, such as a keyhole, oval, circular or rectangular shape.

Figure 15:
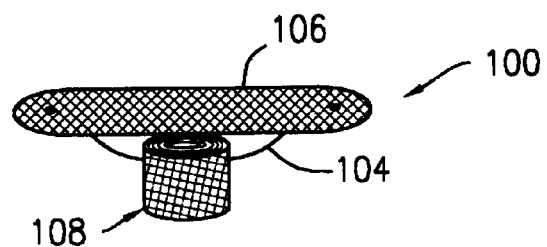
FIG. 15 is a perspective view of a prosthesis according to yet another embodiment of the present invention.

FIG. 15 shows a prosthesis 100 having a similar overall configuration and features as that shown and described above in reference to FIG. 14, viz., with an overlay patch 106 and attachment filament 104. In the embodiment shown in FIG. 15, the element used to fill the facia defect is a generally cylindrical roll 108 of surgical mesh material that is slidable relative to the patch 106 via filament 104.

Figure 16:
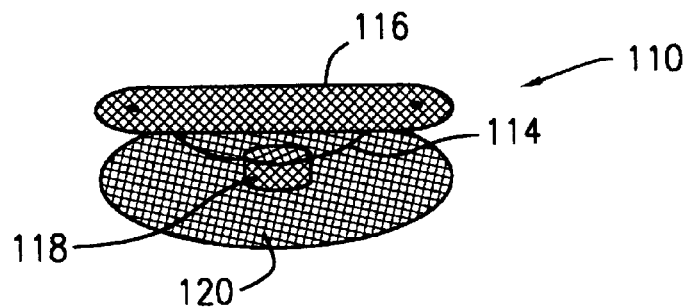
FIG. 16 is a perspective view of a prosthesis according to still another embodiment of the present invention.

FIG. 16 shows a prosthesis 110 having an overlay patch 116, an attachment filament 114 and an underlay patch 120 having a generally cylindrical upstanding prominence 118 that is thermoformed therein for insertion into the facia defect. The filament 114 passes through the prominence 118 to secure the underlay patch 120 to the overlay patch 116 in slidably adjustable relationship thereto, such that the underlay patch may be positioned on the posterior side of the hernia with the prominence 118 extending anteriorly into the facia void. The overlay patch 116 can then be positioned on the anterior side of the herniated facia for optimal surgical attachment. As yet a further alternative, the prominence 118 can be eliminated such that the underlay patch 120 is simply flat. In that case, the filament 114 would simply enter the proximal surface of the underlay patch, extend a selected distance along the distal surface, pass through the distal surface to reemerge through the proximal surface forming a loop to hold the underlay patch in association with the overlay patch 116.

It will be understood that the embodiments described herein are merely exemplary and that a person skilled in the art may make many variations and modifications without departing from the spirit and scope of the invention. All such variations and modifications are intended to be included within the scope of the invention as defined in the appended claims.

I claim:

1. A hernia repair prosthesis, comprising:
   an occlusive member for aiding in the occlusion of a defect in facia tissue;
   an overlay sheet surgically attachable to a first side of the facia tissue;
   a filament extending from a first point of attachment to said overlay sheet to a second point of attachment, said filament extending substantially parallel to said overlay sheet between said first and second points of attachment, said occlusive member slidably attached to said filament to permit said occlusive member to assume a selected position relative to said overlay sheet between said first and second points of attachment.

2. The prosthesis of claim 1, wherein said occlusive member is expandable having a non-expanded configuration with a first radial dimension and an expanded configuration with a second radial dimension larger than said first radial dimension.

3. The prosthesis of claim 2, wherein said occlusive member includes a pleated cone-shaped member.

4. The prosthesis of claim 3, wherein said filament passes through said cone-shaped member proximate to a base thereof, said base being positioned near to said overlay sheet when said prosthesis is used in hernia repair.

5. The prosthesis of claim 3, wherein said occlusive member includes a pair of pleated, cone-shaped members joined at the bases thereof and further comprising means to draw the apexes of said cone-shaped members towards one another, said filament extending through one of said cone-shaped members proximate the apex thereof.

6. The prosthesis of claim 4, wherein said occlusive member and said overlay sheet are composed of surgical mesh.

7. The prosthesis of claim 6, wherein said surgical mesh is biodegradable.

8. The prosthesis of claim 1, wherein said occlusive member is a substantially flat underlay sheet of surgical mesh positionable proximate a second side of the facia.

9. The prosthesis of claim 8, wherein said underlay sheet has a prominence formed therein through which said filament extends and which is extendable into the defect in the facia tissue.

10. The prosthesis of claim 9, wherein said prominence is thermoformed into said underlay sheet.

11. The prosthesis of claim 1, wherein said occlusive member is a generally cylindrical roll of surgical mesh.

12. The prosthesis of claim 11, wherein said filament passes through said roll approximately perpendicularly relative to an axis of said roll, proximate one end thereof.

13. The prosthesis of claim 1, wherein said occlusive member and said overlay sheet are formed of biodegradable surgical mesh.

14. The prosthesis of claim 1, wherein said filament includes a plurality of filaments, said plurality of filaments being substantially parallel to one another.

15. A method of repairing a defect in facia tissue using a prosthesis having an occlusive member for aiding in the occlusion of the defect, an overlay sheet surgically attachable to a first side of the facia tissue and a filament extending from a first point of attachment to the overlay sheet to a second point of attachment, the filament extending substantially parallel to the overlay sheet between the first and second points of attachment, the occlusive member slidably attached to the filament to permit the occlusive member to assume a selected position relative to the overlay sheet between the first and second points of attachment, comprising the steps of:
   (a) positioning the occlusive member proximate the defect in the facia tissue;
   (b) selectively positioning the overlay sheet on the first side of the facia tissue; and
   (c) attaching the overlay sheet to the facia tissue.

16. The method of claim 15, wherein said step of positioning includes sliding the filament through the occlusive member.

17. The method of claim 16, further including the steps of determining the orientation of the filament and adjusting the orientation of the filament prior to attaching.

18. The method of claim 17, wherein said step of adjusting includes rotating said occlusive member to a selected orientation.

19. A prosthesis for herniated tissue having a first side, a second side and a defect therein, comprising:
   first occluding means for occluding the defect extending proximate the first side of the herniated tissue;
   second occluding means for occluding the defect extending substantially parallel to the second side of the herniated tissue; and
   connecting means for slidably connecting said first occluding means and said second occluding means, said connecting means restricting diverging relative motion of said first and second occluding means and permitting a selected amount of generally parallel relative motion along one axis.

20. The prosthesis of claim 19, wherein said first occluding means is insertable into the defect.

21. The prosthesis of claim 19, wherein said first occluding means extends substantially parallel to the first side of the herniated tissue.

22. The prosthesis of claim 21, wherein said first occluding means has a portion that extends into the defect and toward the second side of the herniated tissue.

* * * * *